(12) United States Patent
Nash

(10) Patent No.: US 8,104,986 B2
(45) Date of Patent: Jan. 31, 2012

(54) LIQUID APPLICATOR

(76) Inventor: Alan E. Nash, Gastonia, NC (US)

( * ) Notice: Subject to any disclaimer, the term of this patent is extended or adjusted under 35 U.S.C. 154(b) by 1102 days.

(21) Appl. No.: 11/572,044

(22) PCT Filed: Jul. 15, 2005

(86) PCT No.: PCT/US2005/025205
§ 371 (c)(1),
(2), (4) Date: Jan. 12, 2007

(87) PCT Pub. No.: WO2006/020057
PCT Pub. Date: Feb. 23, 2006

(65) Prior Publication Data
US 2007/0183835 A1    Aug. 9, 2007

Related U.S. Application Data

(60) Provisional application No. 60/588,879, filed on Jul. 16, 2004.

(51) Int. Cl.
*B43K 5/14*    (2006.01)

(52) U.S. Cl. .......... 401/132; 401/123; 401/125
(58) Field of Classification Search .......... 401/132–135, 401/196, 123, 125; 222/94; 604/3
See application file for complete search history.

(56) References Cited

U.S. PATENT DOCUMENTS

| | | | | |
|---|---|---|---|---|
| 5,490,736 A | * | 2/1996 | Haber et al. | 401/40 |
| 5,558,874 A | * | 9/1996 | Haber et al. | 424/402 |
| 5,660,273 A | * | 8/1997 | Discko, Jr. | 206/229 |
| 5,681,574 A | * | 10/1997 | Haber et al. | 424/402 |
| 6,007,264 A | * | 12/1999 | Koptis | 401/132 |

* cited by examiner

*Primary Examiner* — David Walczak
(74) *Attorney, Agent, or Firm* — Shumaker, Loop & Kendrick, LLP

(57) ABSTRACT

An applicator for a liquid product includes an elongated base having a product cup sized for retaining a single-dose quantity of a liquid product; an applicator cup for receiving an applicator pad; and a channel interconnecting the product cup and the applicator cup. An absorbent applicator pad is disposed in the applicator cup. A liquid product is positively retained in the product cup until it is desired to apply the liquid product.

12 Claims, 3 Drawing Sheets ical, hygiene, and first aid fields. One example of
LIQUID APPLICATOR

BACKGROUND OF THE INVENTION

This invention relates generally to a combined storage package and applicator, and more particularly to a disposable single-dose applicator for a liquid product.

Liquid phase products or "liquid products" have many uses in the medical, hygiene, and first aid fields. One example of such a liquid phase product is a "liquid bandage", that is, a liquid that can be applied to a wound or burn that then cures to form an protective barrier. A liquid bandage can be applied in arbitrary shapes and sizes and can be applied to odd-shaped areas of the body. This saves money and reduces waste compared to fabric or plastic bandages.

This type of product has typically been packaged in multi-dose containers, for example an ordinary glass bottle incorporating a brush applicator. Unfortunately, this kind of package often contains enough liquid for many scores or even hundreds of individual uses or "doses". This arrangement is uneconomical if a user wants to keep the liquid product readily available in several locations (i.e. at home, at work, or in a car). The product is also subject to spoliation, drying out, or breakage well before it is fully consumed. Furthermore, because of the nature of the product, reuse can be unsightly or unappealing. For example, liquid bandages are often applied with an applicator brush that is stored in the bottle after it has been put in contact with an open wound, thereby facilitating contamination of the remaining liquid with wound debris.

There have been attempts in the prior art to create single-dose packages. However, these packages require a separate applicator which is messy and wasteful.

Accordingly, there is a need for a combined single-dose package and applicator.

BRIEF SUMMARY OF THE INVENTION

Therefore, it is an object of the invention to provide a package for a liquid product having a built-in applicator.

It is another object of the invention to provide an applicator which protects a liquid from exposure until it is intentionally opened.

It is another object of the invention to provide an applicator for a single dose quantity of a liquid product.

These and other objects are fulfilled by the present invention, which in one embodiment provides an applicator for a liquid product, including an elongated base which has: a product cup sized for retaining a single-dose quantity of a liquid product; an applicator cup for receiving an applicator pad; and a channel interconnecting the product cup and the applicator cup. An absorbent applicator pad is disposed in the applicator cup. Means are provided for positively retaining a liquid product in the product cup until it is desired to apply the liquid product.

According to another embodiment of the invention, the means for retaining the liquid product include a weak weld formed in the channel between the product cup and the applicator cup.

According to another embodiment of the invention, the base is a sheet-like member having the product cup, applicator cup, and channel formed therein; and a separator sheet is attached to the base so as to enclose the product cup and channel while leaving the applicator cup at least partially exposed.

According to another embodiment of the invention, the base and the separator sheet each are made of a metallic foil; and the base and the separator sheet are bonded together with an adhesive layer.

According to another embodiment of the invention, the weak weld is defined by corresponding portions of the base and the separator sheet aligned with the channel which are attached together less securely than the remainder of the base and the separator sheet.

According to another embodiment of the invention, the applicator extends through an opening in the separator sheet.

According to another embodiment of the invention, the product cup is disposed at a first end of the base and the applicator cup is disposed at a second end of the base.

According to another embodiment of the invention, a portion of the base which surrounds the applicator pad is narrowed so as to expose the applicator pad for convenient use when the cover is opened.

According to another embodiment of the invention, the applicator pad includes a pair of angled sides; and opposed corners of the base at the second end thereof are angled to correspond to the shape of the applicator pad.

According to another embodiment of the invention, opposed corners of the base at the second end thereof are angled to provide access to the applicator pad.

According to another embodiment of the invention, the applicator further includes a cover overlying the applicator pad and removably attached to the applicator, the cover adapted to protect the applicator pad from exposure until the cover is intentionally opened.

According to another embodiment of the invention, a portion of the cover is attached to the applicator more securely than the remainder of the cover so as to define a hinge tab which remains attached to the separator sheet when the remainder of the cover is opened.

According to another embodiment of the invention, the applicator further includes a liquid product disposed in the product cup.

According to another embodiment of the invention, the liquid product is a liquid bandage material.

According to another embodiment of the invention, a method of making an applicator for a liquid product includes: providing an elongated base: molding a product cup sized for retaining a single-dose quantity of a liquid product in the base; molding an applicator cup for receiving an applicator pad in the base; molding a channel interconnecting the product cup and the applicator cup in the base; placing an absorbent applicator pad in the applicator cup; disposing a liquid product in the product cup; and sealing the liquid product in the product cup such that it will be retained therein until it is desired to apply the liquid product.

According to another embodiment of the invention, the step of sealing the liquid product includes forming a frangible divider in the channel between the product cup and the applicator cup.

According to another embodiment of the invention, the method further includes attaching a separator sheet to the base so as to enclose the product cup and channel while leaving the applicator cup at least partially exposed.

According to another embodiment of the invention, the method further includes: providing the separator sheet with a first layer of hot seal adhesive; and providing the base with a second layer of hot seal adhesive; and applying heat and pressure to the separator sheet and the base to bond the adhesive layers together.

According to another embodiment of the invention, the weak weld is formed by bonding a selected area of the base and the separator sheet which is aligned with the channel together, wherein the selected area is bonded together less securely than the remaining bonded portions of the base and the separator sheet.

According to another embodiment of the invention, the method further includes removably attaching to the separator sheet a cover which overlies the applicator pad and protects it from exposure.

According to another embodiment of the invention, the method further includes attaching a portion of the cover to the separator sheet more securely than the remainder of the cover so as to define a hinge tab which remains attached to the separator sheet when the remainder of the cover is opened.

BRIEF DESCRIPTION OF THE DRAWINGS

The invention may be best understood by reference to the following description taken in conjunction with the accompanying drawing figures in which.

DETAILED DESCRIPTION OF THE INVENTION

Figure 1:
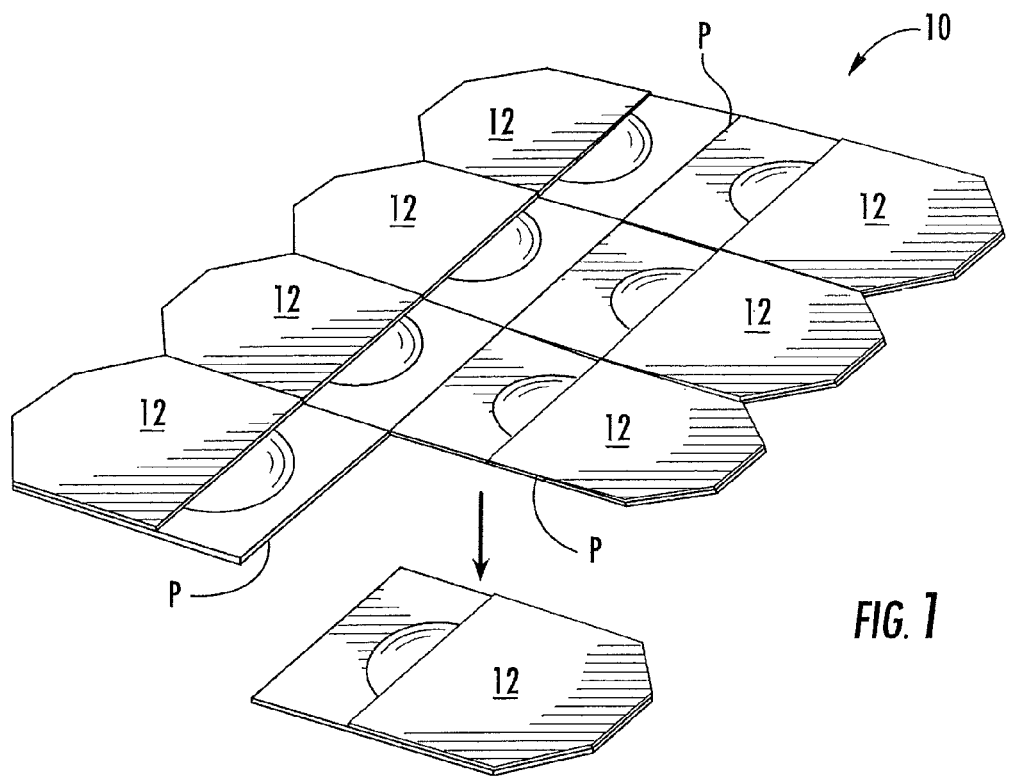
FIG. 1 is a perspective view of a group of applicators constructed in accordance with a preferred embodiment of the present invention.
Figure 2:
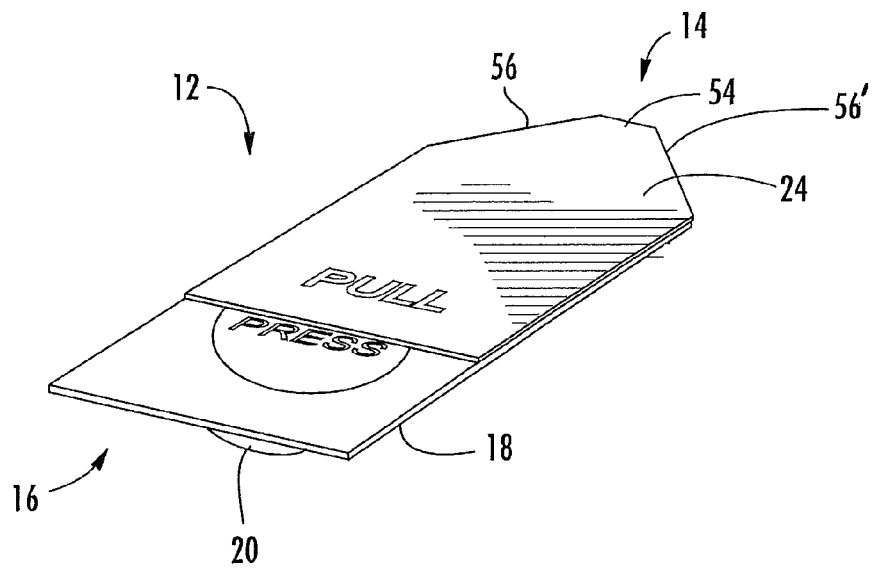
FIG. 2 is an enlarged perspective view of one of the applicators depicted in FIG. 1.

Referring to the drawings wherein identical reference numerals denote the same elements throughout the various views, FIG. 1 depicts a sheet 10 of connected applicators 12. Individual applicators 12 may be separated from the sheet 10 by tearing along perforation lines "P". FIG. 2 shows one of the applicators 12 in more detail. The applicator 12 has first and second ends 14 and 16. Its basic components include a base 18, a product cup 20, and an applicator pad 44 (not visible in FIG. 2), overlaid by a protective cover 24. The product cup 20 contains a selected quantity of a liquid product (not shown). The quantity may be varied as desired to suit a particular application, however in the illustrated example the quantity is sufficient for a single use or "dose" or "application" of the liquid product. As used herein, the term "liquid product" refers to any product in the liquid phase, regardless of its viscosity or chemical characteristics. In the illustrated example, the liquid product is a "liquid bandage" of a known type which cures to create a polymeric seal when applied to a wound.

Figure 3:
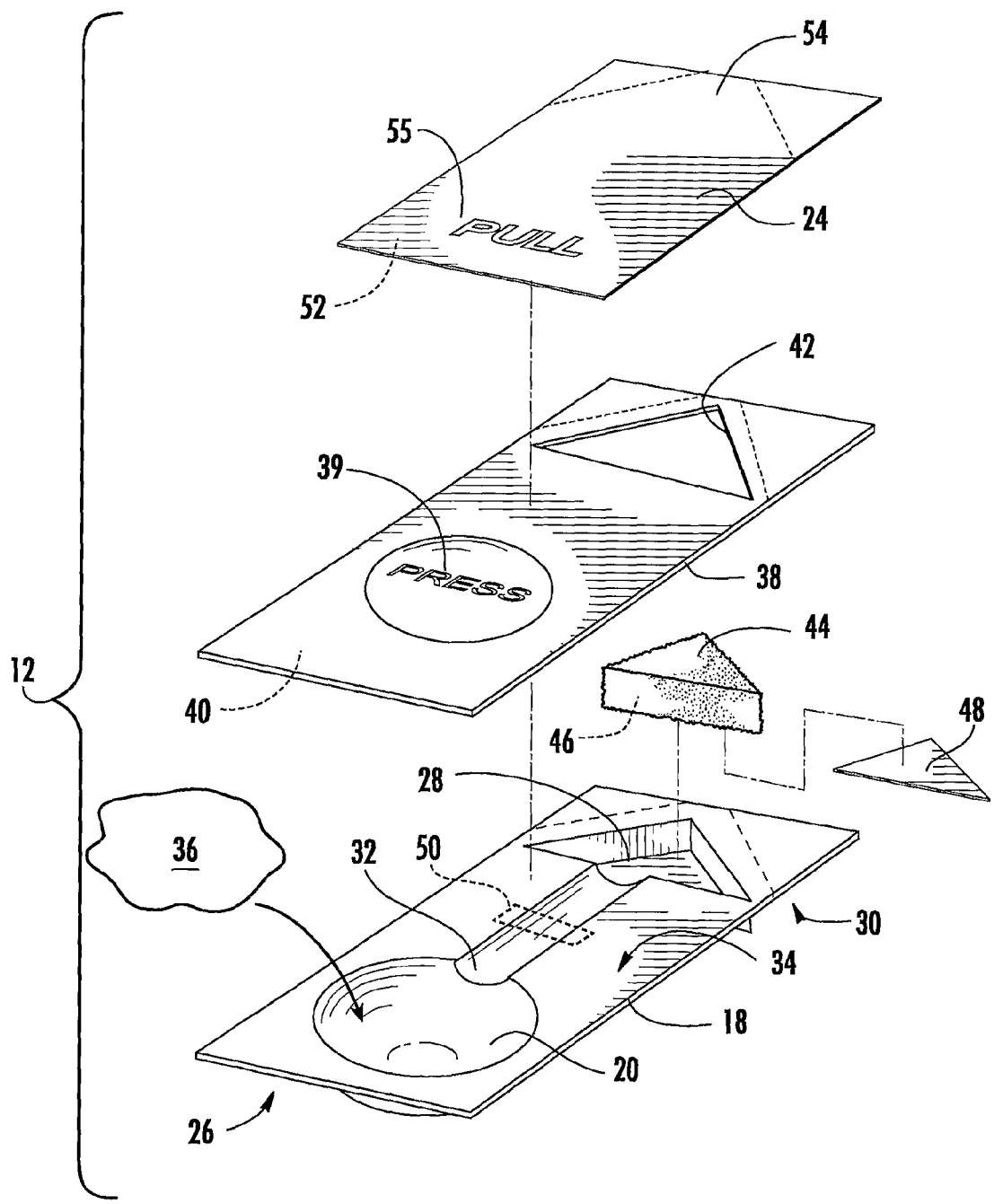
FIG. 3 is an exploded perspective view of the applicator of FIG. 1.

FIG. 3 illustrates the construction of the applicator 12 in more detail. The applicator 12 is built up from multiple layers. The bottom layer is the base 18 which is constructed of a suitable material capable of being molded to shape, resisting the selected liquid product, and excluding air from the liquid product, for example paperboard, plastic, or metal. In the illustrated example the base 18 is constructed from a metallic foil. The concave product cup 20 is molded near a first end 26 of the base 18, and a recessed applicator cup 28 is molded near a second end 30 of the base 18. In the illustrated example, the product cup 20 is generally lozenge-shaped and the applicator cup 28 is generally triangular with planar sides. However, these shapes are not critical and may be varied as desired.

A recessed channel 32 is molded into the base and connects the product cup 20 and the applicator cup 28. A first adhesive layer 34, for example hot seal adhesive of a known type, is applied to the flat portions of the upper surface of the base 18. The product cup 20 is filled with the selected liquid product 36. A separator sheet 38 of a similar shape, size, and composition to the base 18 is coated on its lower surface with a second adhesive layer 40, for example hot seal adhesive of a known type. The separator sheet 38 is placed on top of the base 18 so that the first adhesive layer 34 is in contact with the second adhesive layer 40. The separator sheet 38 may include indicia 39 such as directions for use of the applicator 12. An applicator opening 42, similar in size and shape to the perimeter of the applicator cup 28, is formed in the separator sheet 38. When the separator sheet 38 is placed over the base 18, the applicator opening 42 is aligned with the applicator cup 20 so that the applicator cup 20 is exposed.

An applicator pad 44 is placed in the applicator cup 28. The applicator pad 44 may be constructed of any material which will absorb and retain the liquid product 36, yet allow the liquid product 36 to be transferred to the skin by contact, for example natural or synthetic fibers, paper, sponge, or foam. The applicator pad 44 includes a tacky adhesive coating 46 on the bottom surface thereof which is protected by a release liner 48 until the applicator pad 44 is installed in the applicator cup 28. Alternatively, the applicator pad 44 could be attached to the applicator cup 28 with a separately-applied adhesive.

The separator sheet 38 and the base 18 are sealed together by applying heat and pressure to the mutually contacting surfaces thereof, causing the first and second adhesive layers 34 and 40 to fuse and bond together. This process seals the liquid product 36 in the product cup 20. At the same time, reduced levels of heat and pressure are applied to the base 18 and the separator sheet 38 in an area 50 traversing the channel 32, in order to form a so-called "weak weld" in a known manner. The weak weld closes off the channel 32 and separates the product cup 20 from the applicator cup 28. However, the strength of the adhesive bond at the weak weld is not as strong as the adhesive bond between the remaining portions of the separator 18 and the base 38.

The cover 24, which has a third adhesive layer 52 on a lower surface thereof, is bonded over the separator sheet 38 to cover the applicator pad 44. This bonding operation may take place at the same time as the bonding operation described above, or afterwards. The central portion of the cover 24 at the first end 14 of the applicator 12 is bonded to the separator sheet 38 more securely than the remainder of the cover 24 so as to form a hinge tab 54. The cover 24 may include further indicia 55 thereon, such as instructions for removing the cover 24.

After the bonding operation is complete, the applicator 12 may be trimmed or die-cut to a desired shape. In the illustrated example, the corners 56 and 56' of the first end 14 of the applicator 12 are cut off at an angle (see FIG. 2) so that the applicator pad 44 will be exposed for convenient use when the cover 24 is opened.

The above description has explained the construction process for a single applicator 12. However, it is noted that a plurality of applicators 12 may be produced simultaneously by forming each of the layers (e.g. the base 18, separator sheet 38, and cover 24) in a size sufficient for several individual applicators 12 and performing the above-described assembly steps for a plurality of applicators 12 simultaneously, resulting in sheets 10 of selected numbers of applicators as shown in FIG. 1. The individual applicators 12 may then be separated for use by cutting them apart or otherwise separating them along perforations P.

Figure 4:
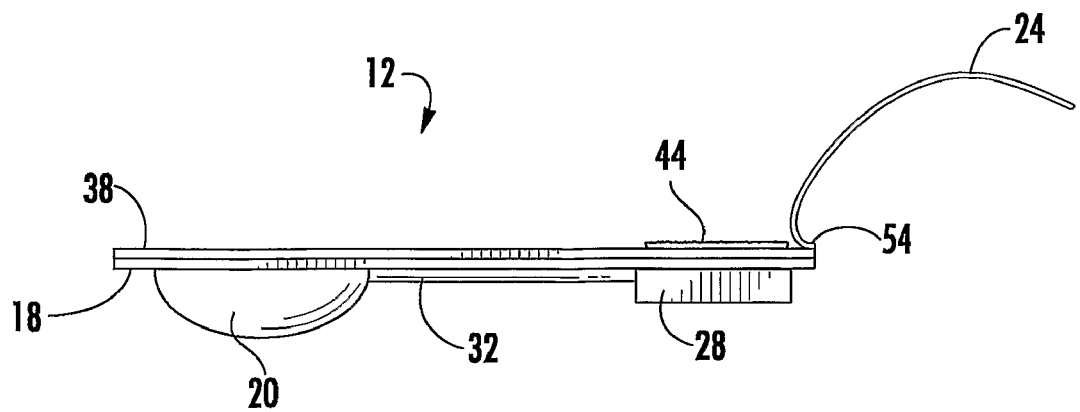
FIG. 4 is a side view of an applicator ready for use.
Figure 5:
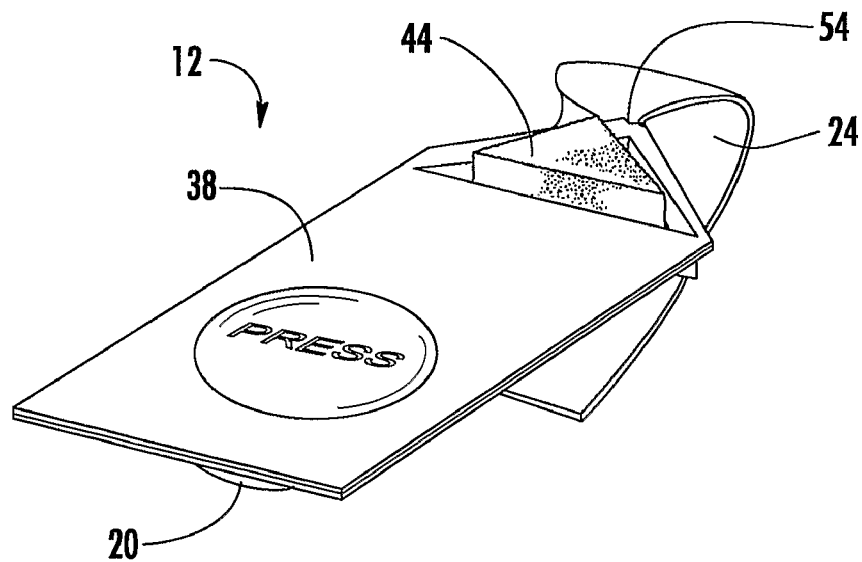
FIG. 5 a perspective view of the applicator of FIG. 4.

The applicator 12 is used as follows. First, the applicator 12 is removed from the external packaging (if present) and separated from the other applicators 12. The cover 24 is then grasped, peeled back, and folded behind the base 18, exposing the applicator pad 44, as shown in FIGS. 4 and 5. The hinge tab 54 retains the cover 24 attached to the applicator 12. The product cup 20 is then pressurized by squeezing it and pressing on the area marked by the indicia 39. The pressurized liquid product 36 breaks the weak weld and flows through the channel 32 into the applicator cup 28, where it saturates the applicator pad 44. The applicator pad 44 may then be used to apply the liquid product 36 to a desired area, for example a burn or wound, by using the applicator 12 as a handle. Once the application is complete, the applicator 12 may be discarded or recycled, leaving a minimal amount of waste packaging.

The foregoing has described a liquid applicator and a method for its production. While specific embodiments of the present invention have been described, it will be apparent to those skilled in the art that various modifications thereto can be made without departing from the spirit and scope of the invention. Accordingly, the foregoing description of the preferred embodiment of the invention and the best mode for practicing the invention are provided for the purpose of illustration only and not for the purpose of limitation.

What is claimed is:

1. An applicator for a liquid product, comprising:
an elongated base which includes:
  a product cup sized for retaining a single-dose quantity of a liquid product;
  an applicator cup for receiving an applicator pad;
  a channel interconnecting the product cup and the applicator cup;
  an absorbent applicator pad disposed in the applicator cup;
  a separator sheet for positively retaining a liquid product in the product cup until it is desired to apply the liquid product; and
  a cover bonded over the separator sheet to cover the absorbent applicator pad;
wherein the base is a sheet-like member having the product cup, applicator cup and channel formed therein;
wherein the separator sheet is attached to the base so as to enclose the product cup and channel while leaving the applicator cup at least partially exposed; and
wherein the applicator extends through an opening the separator sheet.

2. The applicator of claim 1 wherein the separator sheet for retaining the liquid product comprises a weak weld formed in the channel between the product cup and the applicator cup.

3. The applicator of claim 1 wherein:
the base and the separator sheet each comprise a metallic foil; and
the base and the separator sheet are bonded together with an adhesive layer.

4. The applicator of claim 1 wherein a weak weld is defined by corresponding portions of the base and the separator sheet aligned with the channel which are attached together less securely than the remainder of the base and the separator sheet.

5. The applicator of claim 1 wherein the product cup is disposed at a first end of the base and the applicator cup is disposed at a second end of the base.

6. The applicator of claim 5 wherein a portion of the base which surrounds the applicator pad is narrowed so as to expose the applicator pad for convenient use when the cover is opened.

7. The applicator of claim 5 wherein:
the applicator pad includes a pair of angled sides; and
opposed corners of the base at the second end thereof are angled to correspond to the shape of the applicator pad.

8. The applicator of claim 5 wherein opposed corners of the base at the second end thereof are angled to provide access to the applicator pad.

9. The applicator of claim 1, wherein the cover is removably attached to the applicator and is adapted to protect the applicator pad from exposure until the cover is intentionally opened.

10. The applicator of claim 7 wherein:
a portion of the cover is attached to the applicator more securely than the remainder of the cover so as to define a hinge tab which remains attached to the separator sheet when the remainder of the cover is opened.

11. The applicator of claim 1 further comprising a liquid product disposed in the product cup.

12. The applicator of claim 11 wherein the liquid product is a liquid bandage material.

* * * * *

UNITED STATES PATENT AND TRADEMARK OFFICE
CERTIFICATE OF CORRECTION

| | | |
|---|---|---|
| PATENT NO. | : 8,104,986 B2 | Page 1 of 1 |
| APPLICATION NO. | : 11/572044 | |
| DATED | : January 31, 2012 | |
| INVENTOR(S) | : Alan E. Nash | |

It is certified that error appears in the above-identified patent and that said Letters Patent is hereby corrected as shown below:

IN THE CLAIMS:

Column 5, line 42, claim 1, after the word opening, enter the word in.

Signed and Sealed this
Thirteenth Day of March, 2012

David J. Kappos
*Director of the United States Patent and Trademark Office*